United States Patent

Lee

Patent Number: 5,330,420
Date of Patent: Jul. 19, 1994

[54] HEMOLYSIS DETECTOR

[75] Inventor: Kyu H. Lee, Bryn Mawr, Pa.

[73] Assignee: Therakos, Inc., Westchester, Pa.

[21] Appl. No.: 820,102

[22] Filed: Jan. 13, 1992

[51] Int. Cl.$^5$ .............................................. A61N 1/00
[52] U.S. Cl. ........................................... 604/4; 609/6; 210/646
[58] Field of Search ................. 604/4, 5, 6; 210/645, 210/646, 650, 745, 747, 929

[56] References Cited

U.S. PATENT DOCUMENTS

| | | | |
|---|---|---|---|
| 1,943,684 | 1/1934 | Martin et al. | 210/745 X |
| 3,705,100 | 12/1972 | Blatt et al. | 210/23 |
| 3,799,672 | 3/1974 | Vurek | 604/4 X |
| 3,848,580 | 11/1974 | Hyden et al. | 128/2 F |
| 3,979,290 | 9/1976 | Löffler | 210/745 |
| 4,116,832 | 9/1978 | Tardivel | 210/745 |
| 4,128,313 | 8/1980 | Aid et al. | 210/650 |
| 4,136,818 | 1/1979 | Larrabee | 604/4 X |
| 4,191,182 | 3/1980 | Popovich et al. | 128/214 |
| 4,350,156 | 9/1982 | Malchesky et al. | 128/214 |
| 4,374,731 | 2/1983 | Brown et al. | 210/637 |
| 4,466,804 | 8/1984 | Hino | 604/4 |
| 4,735,613 | 4/1988 | Bellin et al. | 604/141 |
| 4,762,620 | 8/1988 | Sama | 210/929 X |
| 4,807,886 | 9/1989 | Botkins, Jr. | 210/745 X |
| 5,116,308 | 5/1992 | Hagiwara | 604/4 |

FOREIGN PATENT DOCUMENTS 0112094 6/1984 European Pat. Off. .
0217624 4/1987 European Pat. Off. .

OTHER PUBLICATIONS

Patent Abstracts of Japan, vol. 13, No. 162 (P-859) Apr. 19, 1989 & JP-A-62 000 450 (Terumo Corp Inc.) Jan. 5, 1989.
Patent Abstracts of Japan, vol. 12, NO. 350 (P-760) Sep. 20, 1988 & JP-A-63 103 945 (Toshiba Corp) May, 9, 1988.
Patent Abstracts of Japan, vol. 11, No. 164 (P-580) May 27, 1987 & JP-A-62 000 838 (Kawasumi Lab Inc.) Jan. 6, 1987.

*Primary Examiner*—Robert A. Hafer
*Assistant Examiner*—Sam Rimell
*Attorney, Agent, or Firm*—Joel R. Petrow

[57] ABSTRACT

An apparatus and method are disclosed for continuous, on-line monitoring of extracorporeal blood in a blood path. A shell has a blood inlet port, a blood outlet port and two compartments: a blood compartment and a plasma compartment separated by a semi-permeable membrane that allows plasma to pass, but not red blood cells. Blood flows through the blood compartment and transmembrane pressure is applied between the blood and the plasma compartments causing the plasma inside the plasma compartment to be replaced by fresh plasma that is flowing through the blood compartment. Any color change of the plasma in the plasma compartment can be detected.

3 Claims, 2 Drawing Sheets

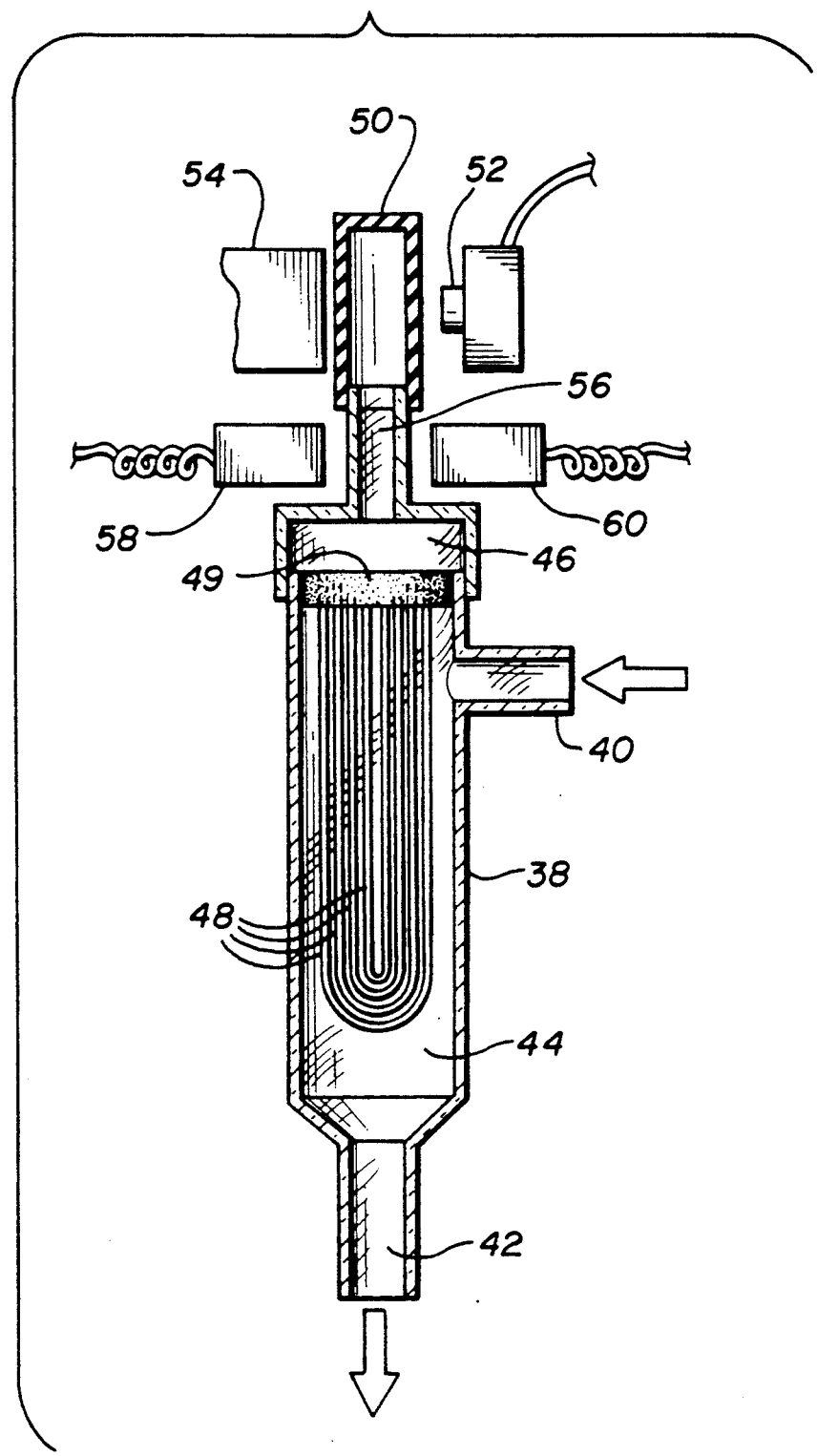

HEMOLYSIS DETECTOR

BACKGROUND OF THE INVENTION

Handling of the blood outside the body, referred to as extracorporeal, is frequently used in medical procedures in treatments such as blood-oxygenation, plasmapheresis, leukopheresis, hemopheresis, extracorporeal chemotherapy, hyperthermia, hypothermia, bone marrow transfusions, blood transfusions processing by heart lung machines during surgery and dialysis for patients with kidney failure. In such procedures there is always a risk that homolysis, or the breaking of red blood cells, may occur.

As is known to those practicing the art, the breaking of blood cells is deleterious not only from the loss of the function of those cells, but also by the release into the blood plasma of hemoglobin which is toxic.

Heretofore, in hemodialysis, hemoperfusion, blood transfusion and other extracorporeal blood therapies, whether hemolysis occurred was determined by taking blood samples and subjecting them to analysis. This is typically done by taking the sample to a laboratory to separate red blood cells from plasma and looking for the artifacts of hemolysis, such as hemoglobin, in the plasma.

This approach is not usually satisfactory because of the damage that can be done to a patients blood while the test is being performed. It is also possible that hemolysis may occur to a significant degree between the time in which the tests are performed.

Currently there is no system available for on-line hemolysis detection. It is, therefore, impossible to have continuous, on-line detection of hemolysis in a red blood containing components such as packed blood cells, buffy coat or whole blood in a blood line. Hemolyzed blood is dangerous to the patient due not only loss of blood cells, but more importantly the toxic effects of free hemoglobin.

Detection of hemolysis in plasma is further complicated by the fact that the characteristics of plasma, in particular color, vary from individual to individual and varies for a single individual over time depending of such factors as diet, and other metabolic differences that manifest themselves in the blood.

While the prior art has concerned itself with methods and apparatus for separation of blood components, these have not been employed to detect hemolysis on a real-time, continuous basis.

For example, U.S. Pat. No. 3,705,100 to Blatt et al. describes a method and apparatus for fractionating blood in order to separate the blood components that may be desirable in blood transfusions. Taught is the use of centrifugal separation techniques and the use of a filtration membrane such as anisotropic and depth filter membranes. This allows the plasma component of blood to be used in an emergency while the formed elements of the blood such as red blood cells, white blood cells, and platelet are returned to the donor so that more frequent bleedings can be taken.

U.S. Pat. No. 4,191,182 to Popovich, et al. describes a method and apparatus for plasmapheresis. Again, the system described employs a membrane with the appropriate pore sized to fractionate blood into cellular and plasma components. This reference particularly points out that flow rates are important to attaining the desired result using the specified sheer stresses and pressures on the membrane ultra filter.

U.S. Pat. No. 4,350,156 to Malchesky, et al. describes a continuous, on-line system and apparatus for removing macromolecules from a physiological fluid such as blood. Membranes are employed in a blood flow path to separate blood plasma, cellular components, and macromolecules that are associated with progress of a variety of diseases. Removal of these molecules inhibits the progress of certain diseases.

U.S. Pat. No. 4,374,731 to Brown, et al. describes a method and apparatus for performing plasmaphereses while controlling the plasma collection rate through a plasmapheresis membrane filter. By regulating the pressure on the plasmapheresis membrane filter, the flow of plasma therebetween can be controlled.

The goal of these prior art patents is to separate as much plasma as possible from the blood for therapeutic or collection purposes. Therefore, these membranes plasmapheresis devices normally have a membrane surface area in the range of several thousand square centimeters in a plasma port in the plasma compartment through which the plasma can be collected for removal or further treatment before it is returned back to the patient.

It is an object of the present invention to provide an on-line device that can continuously detect hemolysis that may be developing in a blood path. It is a further object that such device be capable of performing without attention or replacement.

It is another object of the invention to provide a device that does not require careful manual calibration, adjustment or interpretation to distinguish between variabilities in normal blood plasma among people or between an individual's blood at different times.

Another object of the present invention is to provide a device that is simple and sufficiently inexpensive that the portion of the device in contact with the patient's blood is disposable so that contamination between patients is eliminated.

SUMMARY OF THE INVENTION

The above objects are realized by a device comprising a shell having a blood inlet port receiving blood, a blood outlet port for returning blood to the blood path and two compartments, a blood compartment and a plasma compartment separated by a semi-permeable membrane. The semi-permeable membrane allows plasma to pass, but not red blood cells. The blood inlet and outlet ports located in the blood compartment allows a passage of at least a representative of portion of the blood flowing through the main blood path to go through the blood compartment of the shell. An elastic air sac is contiguous with plasma compartment in order to periodically apply a transmembrane pressure. The plasma compartment has an optical window formed along a portion of the shell through which the plasma optical characteristics can be evaluated by the transmission or reflection. The semi-permeable membrane allows plasma to permeate, but not red blood cells. In application, blood flows through the blood compartment and transmembrane pressure is generated between the blood and the plasma compartments by periodically squeezing and releasing the elastic air sac. Because of the alternating change in high and low pressure sides between the blood and plasma compartments the plasma inside the plasma compartment is always replaced by fresh plasma that is flowing as part of the blood through the blood compartment. After an initial optical measurement is made, for instance using a light source and photo detector with the appropriate filters, any color change in the plasma can be detected and presented either as a numerical value or by tripping an alarm at a predetermined set point.

DESCRIPTION OF THE DRAWINGS

FIG. 4 is a cross sectional view of a alternate embodiment of the present invention.

DETAILED DESCRIPTION OF THE PREFERRED EMBODIMENT

Figure 1:
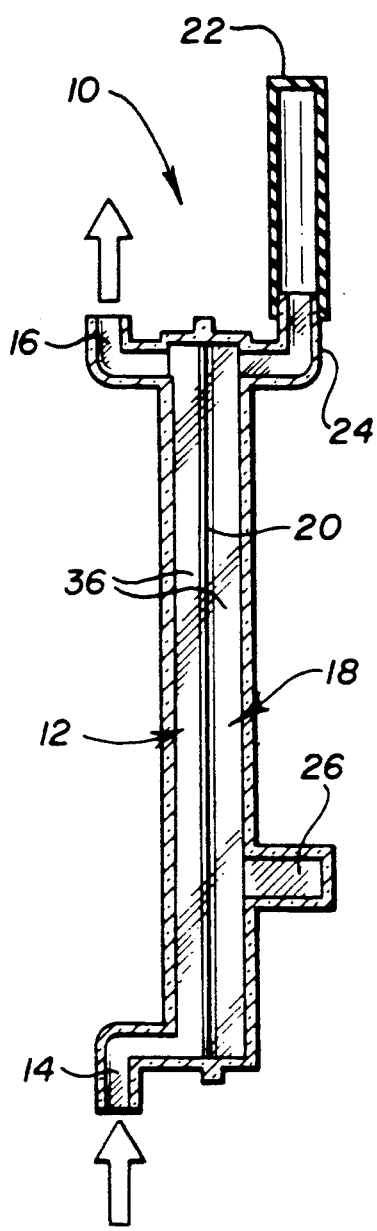
FIG. 1 shows a longitudinal cross section of the blood-containing device of the present application.

Referring now to FIG. 1 shown is an outer shell 10 of the blood-containing device which is preferably made from one or more clear polymers. Acceptable polymers are those such as acrylic, polystyrene or polyvinylchloride. The main criteria for such a housing is that it be fairly rigid, inert when exposed to blood and be substantially transmissive of light at least one frequency.

This shell 10 is divided into a blood compartment 12 having an inlet port 14 and outlet port 16. The inlet port 14 receives a flow of blood from an extracorporeal blood path or blood path so that the blood flows into the blood compartment 12 then exits the compartment through outlet port 16 to rejoin the blood flowing through the blood path or blood path.

Dividing the blood compartment 12 from a plasma compartment 18 is membrane 20. The membrane is of the microporous type having a pore size distribution and arranged such that it allows only plasma to permeate the membrane and remain impenetrable to any cellular elements. The pore distribution should typically be within 0.1 to 2.0 microns. An example of a membrane having acceptable perimeters and characteristics is Thermopore 800, manufactured by Gelman Sciences of Ann Arbor, Mich.

Because cellular components of the blood cannot penetrate membrane 20, only the plasma component of the blood including that of lysed cells will be found in plasma compartment 18. Included in the plasma component of the blood are the remnants of red blood cells that have been lysed or undergone hemolysis. Included in these remnants of red blood cells is hemoglobin which gives blood its characteristic red color from oxygenated iron.

Contiguous with plasma compartment 18 is air sac 22 which is connected to the plasma compartment 18 by air sac neck 24. The elastic air sac 22 is preferably made of elastic material such as silicone rubber, polyurethane, PVC or other elastomers.

The purpose of the elastic air sac is to allow a differential pressure to be applied to contents of plasma compartment 18 exerting differential pressure across membrane 20. The reason for applying this pressure difference will be explained below.

Also contiguous with plasma compartment 18 is light path chamber 26.

Figure 2:
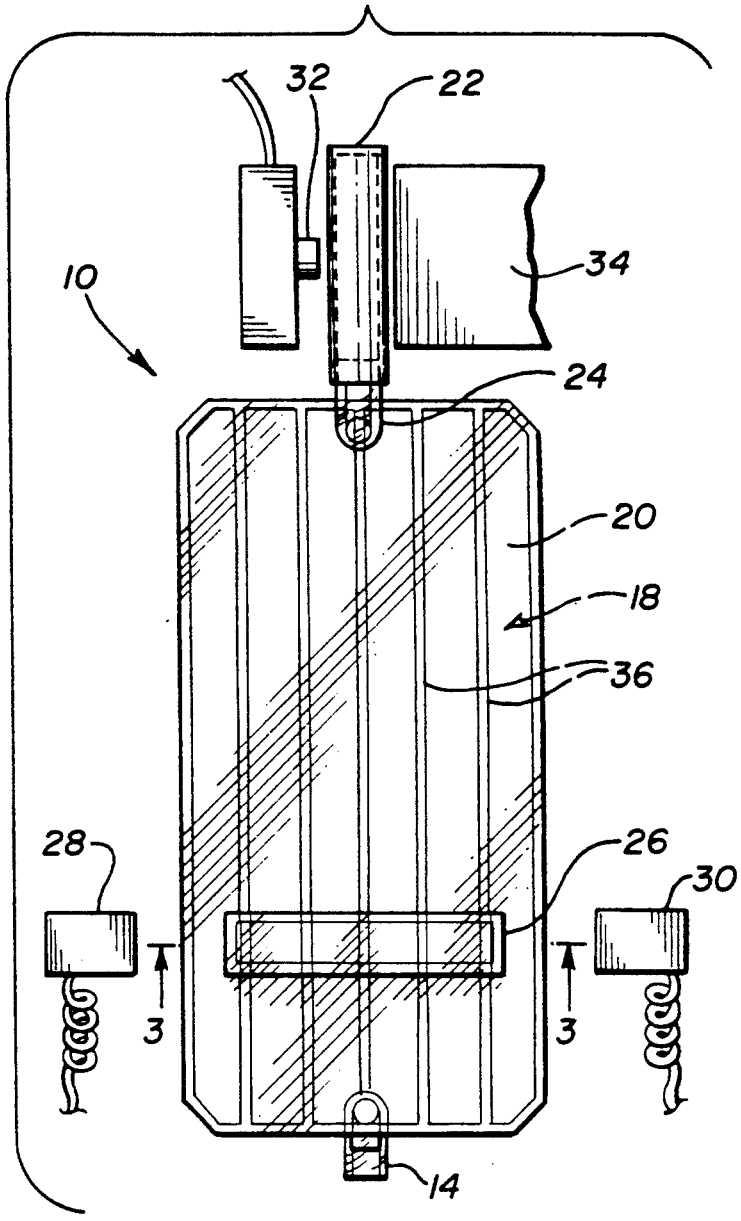
FIG. 2 shows a top plan view the present invention including the blood-containing device of FIG. 1, the optical detection system and the means for applying periodic pressure to the elastic air sac.

Referring now to FIG. 2, the device of FIG. 1 is shown in a top plan view along with associated apparatus. Continuing the description of the light path chamber 26, it is shown with the associated light source 28 and optic sensor 30. As can be readily determined from the figure, light for instance in the green region with a wavelength of 500 to 700 nm, from light source 28 passes through a quantity of plasma contained in light path chamber 26 where upon a certain amount of light is absorbed before detection by optic sensor 30.

Also shown is elastic air sac 22 as described in the previous figure along with means for compressing and relaxing the elastic sac. Plunger 32 applies force on the elastic air sac 22 against a fixed member 34. This is done by applying power to plunger 32 to compress air sac 22 then terminating the power to the plunger to relax the force on the elastic air sac.

Figure 3:
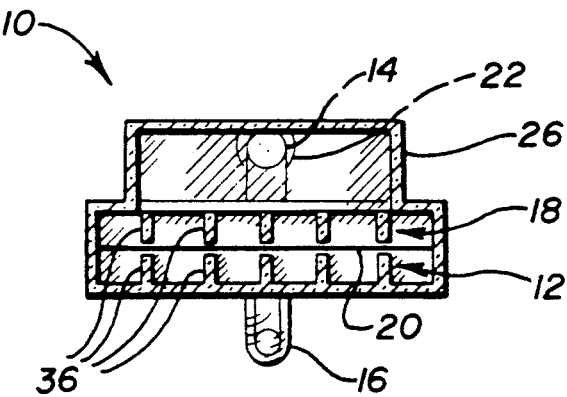
FIG. 3 shows the device in cross section perpendicular to that of FIG. 1, through line 3—3 of FIG. 2 which includes the plasma compartment optical portion.

Referring now to FIG. 3, the device of FIG. 1 with outer shell 10 in FIG. 2 is shown in a cross-section through line 3—3.

In addition to blood compartment 12, plasma compartment 18 and light path chamber 26, also shown are membrane support ribs 36. These support ribs hold membrane 20 in place between the blood compartment and plasma compartment and support the membrane, preventing it from shifting as the transmembrane pressure fluctuates such that the membrane does not excessively bow and tear.

In application, the device 10 is connected to any portion of a blood path or blood path. The elastic air sac 22 is compressed by the plunger 32 or by other means to expel air in the plasma compartment into the blood compartment. After the blood path is primed with priming solution, such as normal saline or Ringer solution, the pressure on the elastic air sac is relaxed creating negative pressure inside the plasma compartment and drawing the priming liquid across the membrane into the plasma compartment.

As patient treatment commences and blood replaces the priming solution, the elastic air sac is compressed by plunger 32 and periodically released. This compression/relaxing action for example, every 2 minutes, periodically replaces the liquid inside the plasma compartment with new plasma from the blood compartment.

Light transmittance in the green region at 500–700 nm, (or alternately reflectance) through the light path chamber 26 is measured by the optic sensor such as photocell 30.

An initial reading is taken to determine the nonhemolyzed transmission of the patient's blood plasma. During patient treatment if any hemolysis develops, hemoglobin in the plasma appears in the plasma compartment and changes the light transmission or reflectance through the light path chamber 26.

Hemolysis can be detected in the line immediately and the appropriate action taken to protect the patient.

As alternate embodiments, the elastic air sac could be replaced by a disposable syringe and plunger activator. Other possible embodiments employ the use of flexible polycarbonate, acrylic, PVC, or TPX as the material for making the shell 10. In such a design transmembrane pressure is generated by squeezing the shell 10, itself rather than utilizing a separate elastic air sac.

An apparatus incorporating the present invention was constructed and tested as follows:

The outer shell was made of transparent acrylic housing and Thermopore 800 by Gelman Sciences was used as the membrane separating the blood compartment from the plasma compartment.

For this particular test device, a small PVC tubing with a slide clamp was attached to the plasma compartment side of the outer shell and contiguous with that compartment. This was done in order to be able to expel the air inside the plasma compartment during initial priming.

After the device was primed with normal saline, bovine blood was pumped through the blood compartment. While pumping the blood through the device, distilled water was injected into the incoming blood line to burst blood cells. After about three minutes, red color plasma appeared in the plasma compartment, indicative of hemolysis. When the test was repeated and the device was squeezed between two fingers to generate transmembrane pressure between the blood and plasma compartments, a reddish color appeared in the plasma compartment almost immediately.

A similarly successful device was made incorporating a hydrophobic membrane in place of the PVC tubing for venting air from the plasma compartment. This alternate embodiment also contained a perforated membrane support used to support and protect the membrane and incorporated on the blood compartment side of the membrane.

An alternate embodiment of the present invention is constructed using hollow fiber, microporous membranes instead of a flat sheet membrane.

Referring to FIG. 4, a hemolysis detector constructed according to this embodiment is shown in cross section. As with the other embodiments, there is an outer shell 38, having a blood inlet port 40 and a blood outlet port 42, a blood compartment 44 and a plasma compartment 46. In contrast to the flat membrane of the previous embodiment, however, here are used a plurality of hollow fiber, microporous membranes 48 identical to those used in blood cell/plasma separation and known to those practicing in the art. The hollow fibers number approximately 20 to 30 and serve to separate the blood compartment, bounded by the outer surface of the hollow fibers, from the plasma compartment, bounded by the inner surface of the hollow fibers. In addition to the boundary formed by the hollow fibers, there is an additional barrier between the compartments and its support means for the fibers, such as potting compound, 49.

The remainder of the device is identical in function and similar in construction to the first embodiment, having an elastic air sac 50 and plunger 52 to apply force on the air sac 50 against fixed member 54.

In this embodiment, the air sac neck and light path chamber, are combined in a single element 56. The transmembrane pressure supplied by the squeezing of the elastic air sac, transverses the path 56 longitudinally while the light generated by light source 58 traverses the pathway 56 before being received by the optical sensor 60.

Although the construction of this embodiment is similar and the operation is identical, the embodiment using hollow fiber microporous membranes has the advantage of a larger membrane area in a similarly-sized device. This results in a device which is more efficient in the exchange of plasma across the membrane than an equal-sized device using a flat sheet.

I claim:

1. A device for the detection of hemolysis of red cells in blood in an extracorporeal blood path comprising:
    a shell, said shell divided into a blood compartment and a plasma compartment,
    a blood inlet port for receiving a flow of blood into the blood compartment of said shell from said extracorporeal blood path,
    a semipermeable membrane permeable to blood plasma but impermeable to blood cells acting as the boundary between the blood compartment and the plasma compartment,
    means for applying a varying transmembrane pressure between the blood and plasma compartments comprising an elastic air sac contiguous with said plasma compartment,
    detection means for determining optical changes associated with the presence of lysed red blood cells in the blood plasma portion of the blood in the plasma compartment of said shell, and
    a blood outlet port for returning said flow of blood from the blood compartment of said shell to said extracorporeal blood path.

2. A method of detecting hemolysis in an extracorporeal blood path comprising:
    taking a portion of blood flow from said extracorporeal blood path,
    passing said portion of blood through a blood compartment, at least one wall of which is a semipermeable membrane capable of passing blood plasma but not blood cells,
    applying a varying transmembrane pressure across said semi-permeable membrane,
    separating at least some of the blood plasma from the remainder of said blood through said semi-permeable membrane,
    collecting said separated plasma in a plasma compartment,
    measuring optical changes associated with the presence of lysed red blood cells in the blood plasma collected in the plasma compartment, and
    returning the portion of blood taken and passed through said blood compartment to said extracorporeal blood path.

3. The method of claim 2 wherein said pressure is applied by compressing an air sac contiguous with said plasma compartment.

* * * * *